United States Patent [19]

Trittenbass

[11] Patent Number: 4,729,378
[45] Date of Patent: Mar. 8, 1988

[54] APPARATUS FOR ASCERTAINING THE PRESSURE IN A PLENUM CHAMBER

[75] Inventor: Jean Trittenbass, Dübendorf, Switzerland

[73] Assignee: Interzeag AG, Schlieren, Switzerland

[21] Appl. No.: 934,715

[22] Filed: Nov. 25, 1986

[30] Foreign Application Priority Data

Nov. 26, 1985 [CH] Switzerland ................. 05047/85

[51] Int. Cl.⁴ ............................................. A61B 5/10
[52] U.S. Cl. ......................................... 128/645; 128/748; 128/774; 73/79
[58] Field of Search .................... 128/645–652, 128/774, 748; 73/R78–79, 81

[56] References Cited

U.S. PATENT DOCUMENTS

| | | | |
|---|---|---|---|
| 1,423,293 | 7/1922 | Amsler | 128/650 |
| 2,708,928 | 5/1955 | Zenatti | 128/645 |
| 2,882,891 | 4/1959 | Husted | 128/645 |
| 3,628,526 | 12/1971 | Bigliano | 128/645 X |
| 3,630,073 | 12/1971 | Michel | 73/81 |
| 3,714,819 | 2/1973 | Webb | 128/645 |
| 4,159,640 | 7/1979 | Leveque et al. | 128/774 X |
| 4,364,399 | 12/1982 | Dashefsky | 128/774 |
| 4,505,278 | 3/1985 | Alban | 128/645 X |
| 4,628,938 | 12/1986 | Lee | 128/652 |

FOREIGN PATENT DOCUMENTS

| | | | |
|---|---|---|---|
| 0976919 | 3/1951 | France | 128/650 |
| 7408214 | 12/1975 | Netherlands | 128/652 |
| 0663372 | 5/1979 | U.S.S.R. | 128/652 |

OTHER PUBLICATIONS

Zeimer et al., "An Instrument for Self-Measurement of Intraocular Pressure", *IEEE Trans. on Biomed. Engr.*, vol. BME-29, No. 3, 3-1982, pp. 178-183.

*Primary Examiner*—Edward M. Coven
*Assistant Examiner*—Angela D. Sykes
*Attorney, Agent, or Firm*—Peter K. Kontler

[57] ABSTRACT

A tonometer which is used to measure the tension of eyeballs has a first testing device with a first outwardly bulging deformable wall which can be pressed against the eyeball (either directly or by way of the eyelid) and a second flexible wall which is deformable by the flexible or rigid wall member of a second testing device. The housing of the first testing device is filled with a gaseous or liquid fluid whose pressure is monitored by one or more gauges or risers, and a further instrument is provided on or in the second testing device to indicate the position of the wall member. The scale of the further instrument is calibrated in units of pressure in such a way that the tension of the eyeball can be read directly off the scale when the gauges or risers indicate that the deforming work upon one of the flexible walls is the same as that upon the other flexible wall.

16 Claims, 7 Drawing Figures

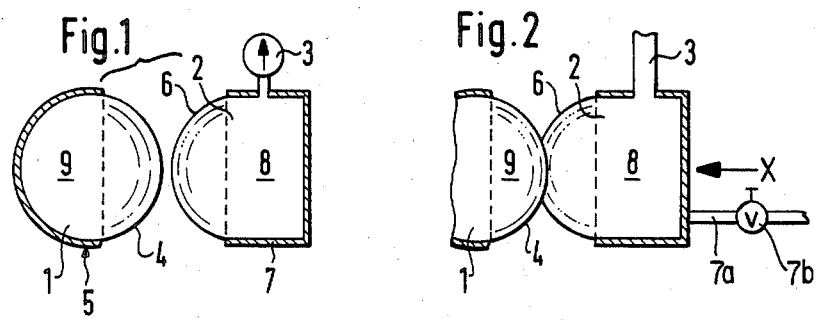
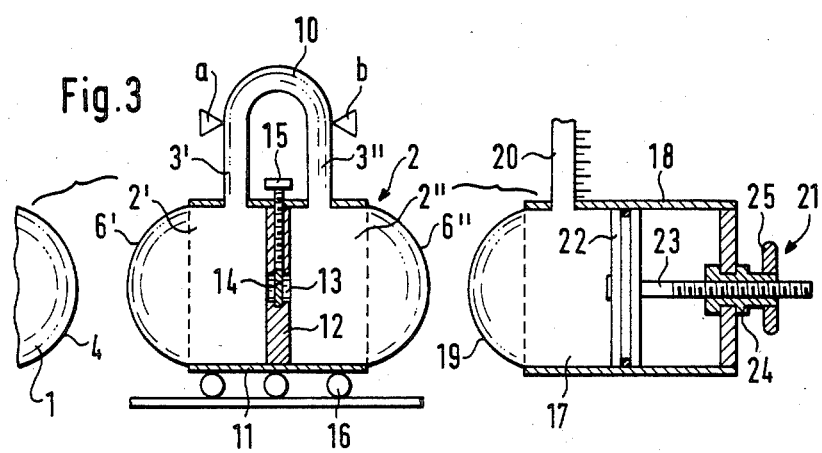
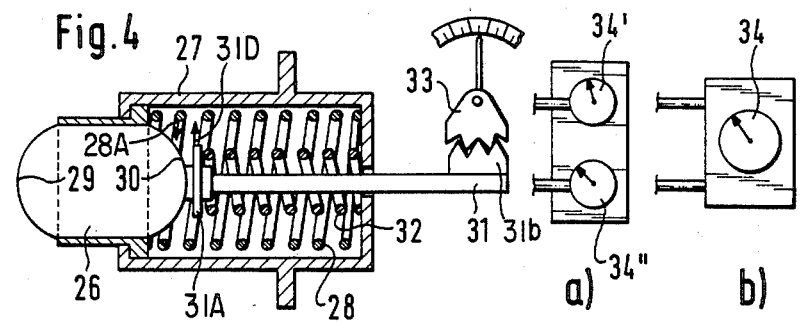

APPARATUS FOR ASCERTAINING THE PRESSURE IN A PLENUM CHAMBER

BACKGROUND OF THE INVENTION

The present invention relates to improvements in apparatus for ascertaining the pressure in a plenum chamber. More particularly, the invention relates to improvements in apparatus for ascertaining the pressure in a plenum chamber without the need for penetrating into the plenum chamber.

The human eyeball can be said to constitute a plenum chamber, i.e., an object having an envelope surrounding an internal space which is maintained above atmospheric pressure. Apparatus for ascertaining the tension of eyeballs are known as tonometers, and the following description will refer primarily to tonometers with the understanding, however, that the apparatus of the present invention can be practiced with equal or similar advantage to ascertain the pressure in other types of plenum chambers wherein the shell or envelope for a body of fluid comprises a flexible portion.

The need for apparatus or instruments which can be used to ascertain the tension of an eyeball without puncturing the eyeball or drilling a hole therein is particularly pronounced in certain branches of ophthalmology. For example, timely treatment of glaucoma (defined as a disease of the eye marked by increased pressure within the eyeball that damages the optic disk and results in gradual loss of vision and ultimate blindness) necessitates the provision of means for measuring the tension of the eyeball. The pressure in a healthy human eyeball is approximately 26.66 mbar (20 mm Hg). The presently known tonometers which are used for such purposes are quite complex, bulky and expensive and, as a rule, can be operated properly only by physicians or by other specially and highly trained persons.

The article on pages 1791/1793 of the November 1983 volume (No. 101) of the publication entitled "Arch Ophtalmol" describes a tonometer which can be manipulated by a patient. In contrast to an electronic tonometer or an electronic tonograph (which is manipulated by a physician or by a highly skilled and trained person and serves to ascertain the magnitude of force which is needed for applanation of the cornea), the tonometer which is disclosed in the aforementioned publication is designed to measure the pressure which is needed to carry out an applanation of the cornea. In either event, it is necessary to reduce the sensitivity of the cornea by administering a pain killer and/or by the application of a thin contact lens.

OBJECTS AND SUMMARY OF THE INVENTION

An object of the invention is to provide an apparatus, particularly a tonometer, which is constructed and assembled in such a way that it can be operated by a patient, or by another unskilled person attending to the patient, without the need for administration of any pain killers and/or for the application of contact lenses.

Another object of the invention is to provide a novel and improved tonometer which can be applied to ascertain the tension of an eyeball while the eyelid remains closed.

A further object of the invention is to provide a tonometer which can be applied without necessitating any preliminary treatment of the cornea.

An additional object of the invention is to provide an apparatus which is constructed and assembled in such a way that it ceases to operate when the force which is applied to effect an applanation of the cornea reaches a predetermined maximum permissible value.

Still another object of the invention is to provide a novel and improved method of measuring the tension of an eyeball or an analogous plenum chamber.

A further object of the invention is to provide novel and improved testing devices which can be used in the above outlined apparatus.

Still another object of the invention is to provide the apparatus with novel and improved means for adjusting the aforediscussed testing devices so as to enable the apparatus to properly measure the tension of eyeballs of patients of all age groups and at different stages of the development of a disease which renders it necessary to monitor the tension at regular or irregular intervals.

An additional object of the invention is to provide a relatively simple, compact and inexpensive tonometer which is affordable to a patient or a healthy person to allow for periodic measurement of the tension of eyeballs.

The invention resides in the provision of an apparatus for ascertaining the pressure in a plenum chamber which has a flexible portion, particularly in the provision of a tonometer for measuring the tension of an eyeball. The apparatus comprises a first testing device which includes a housing having an internal space and comprising first and second mobile walls (e.g., membranes) having outer sides and inner sides. The first testing device further includes means provided in the internal space of the housing to yieldably bias the inner sides of the walls in order to counteract forces which are applied to the outer sides (including a force which is applied to the outer side of the first wall when the latter is pressed against the flexible portion of a plenum chamber), and the apparatus further comprises a second testing device having a mobile member (e.g., a membrane or a rigid pusher or panel) which is operable (e.g., movable) to apply pressure to the outer side of the second mobile wall. The second testing device further comprises means (e.g., a riser or an instrument employing one or more gauges or one or more pivotable pointers) for indicating the pressure which is applied to the outer side of the second wall.

The first testing device preferably further comprises means for indicating the magnitude of forces which act upon the inner sides of the walls.

The biasing means can comprise at least one mechanical spring or one or more fluid-operated springs.

The second testing device can comprise a hollow casing defining an internal compartment, and the mobile member of such second testing device has a first side facing the compartment and a second side which is engageable with the outer side of the second wall. Such second testing device can comprise mechanical or fluid-operated spring means for applying pressure to the first side of the mobile member.

In accordance with a presently preferred embodiment of the invention, the internal space of the housing of the first testing device has a first fluid-filled part which is adjacent the inner side of the first wall and a second fluid-filled part adjacent the inner side of the second wall. The first testing device further comprises means for indicating the magnitude of forces acting upon the inner sides of the walls including first and second risers or gauges communicating with the first and second parts of the internal space of the housing. The means for indicating the magnitude of forces in such first testing device can further comprise a hollow yoke or other suitable means for communicatively connecting the risers to each other outside of the housing.

If the biasing means comprises a spring which bears upon the inner sides of the walls in the housing of the first testing device, the force measuring means can comprise means for indicating the bias of the spring. For example, if the spring is movable in the housing by the first and/or second wall, the means for indicating the bias can comprise means (e.g., a pivotable pointer) for indicating changes in the position of a portion of the spring with reference to a portion of the housing.

The movable member of the second testing device can constitute or comprise a membrane adjacent a body of fluid in the casing of the second testing device, and the pressure indicating means of such testing device can comprise a pressure gauge which is calibrated to indicate the pressure of fluid in the casing in units of pressure. The preferably convex outer side of the membrane can have a radius which matches or approximates the radius of an eyeball.

The walls of the first testing device may but need not have substantially identical outer sides (in undeformed condition of such walls). Means can be provided to limit the extent of movability of at least one of the walls with reference to the housing of the first testing device to thus reduce the likelihood of injury to the eye if the apparatus is used as a tonometer.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 1 is a schematic partly elevational and partly sectional view of an object to be tested and a schematic partly elevational and partly sectional view of a rudimentary apparatus which embodies the invention;

FIG. 2 shows the apparatus of FIG. 1 during measurement of tension in the plenum chamber of the object;

FIG. 3 is a fragmentary elevational view of a plenum chamber and a partly elevational and partly sectional view of an apparatus which comprises two testing devices and embodies the present invention, the two testing devices being shown in positions out of contact with each other and with the object;

FIG. 4 is a similar partly elevational and partly sectional view of a further apparatus wherein a portion of one testing device is received in the casing of the other testing device;

FIG. 4a shows a modified pressure indicating instrument which can be used in or with the second testing device;

FIG. 4b shows another pressure indicating instrument which can be used in or with the second testing device.

DESCRIPTION OF THE PREFERRED EMBODIMENTS

Figure 5:
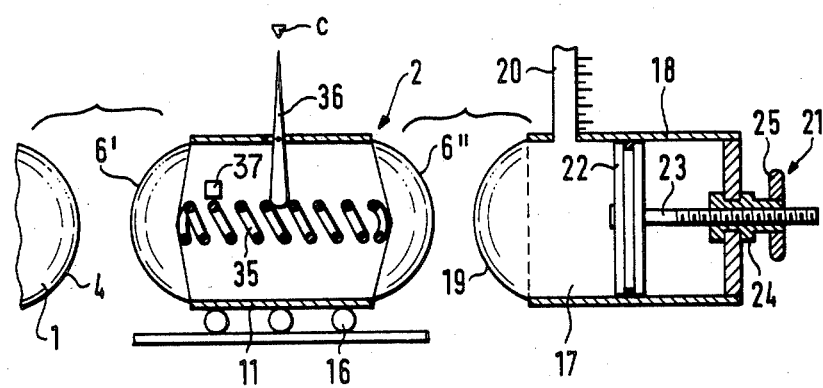
FIG. 5 is a fragmentary elevational view of an object and a partly elevational and partly sectional view of still another apparatus wherein the housing of the first testing device comprises a mechanical spring.

FIGS. 1 and 2 show a rudimentary apparatus which can be used to ascertain the pressure in a plenum chamber 5 of an object 1, e.g., a human eyeball, wherein the body 9 of fluid in the plenum chamber is confined in a substantially spherical envelope having an elastically deformable flexible portion 4. The pressure of the body 9 of fluid in the plenum chamber 5 exceeds atmospheric pressure.

The apparatus of FIGS. 1 and 2 comprises a testing device 2 which includes a rigid or substantially rigid housing 7 defining a fluid-filled internal space 8 and having an elastically deformable flexible wall 6 with a convex outer side and a concave inner side. The wall 6 can constitute a flexible membrane. The apparatus of FIGS. 1 and 2 further comprises an instrument 3 (e.g., a pressure gauge with a suitably graduated scale adjacent a mobile pointer) which serves to ascertain and indicate the magnitude of forces acting upon the inner side of the wall 6. The mean for applying such forces is the body of fluid (e.g., air, another gas or a liquid medium) which fills the internal space 8 of the housing 7. If the internal space 8 is filled with a body of liquid, the illustrated pressure gauge 3 can be replaced with a riser which is provided with or is placed adjacent a suitably calibrated scale so that the person observing the scale can determine the pressure of entrapped liquid.

If the user decides to advance the housing 8 in the direction of arrow X, the outer side of the flexible wall 6 engages and is deformed by the outer side of the flexible portion 4 of the envelope of the plenum chamber 5. This is due to the fact that the pressure of fluid in the internal space 8 is assumed to be less than the pressure of the body 9 of fluid in the plenum chamber 5 of the object 1. Inward deformation of the wall 6 results in a reduction of the volume of the internal space 8 so that the pressure in the space 8 rises and such rise of pressure is indicated by the gauge 3. If the body of fluid in the space 8 is a liquid, the aforementioned riser (such as the riser 3' or 3" of FIG. 3 which then replaces the gauge 3) will contain a correspondingly taller column of liquid.

If the pressure in the space 8 exceeds the pressure of the body 9 of fluid in the plenum chamber 5 before the outer side of the wall 6 engages the plenum chamber 5, the wall 6 deforms the flexible portion 4. The apparatus of FIGS. 1 and 2 is further provided with means (e.g., a hose 7a and a valve 7b in the hose 7a) for permitting controlled gradual evacuation of fluid from or admission of fluid into the space 8. The valve 7b is actuated to permit for evacuation of fluid from the space 8 until the wall 6 and the portion 4 lie flat against each other, i.e., until the wall 6 ceases to make a dent or an inward bulge in the portion 4. The pressure of fluid in the space 8 then matches the pressure of the body 9 of fluid in the plenum chamber 5, and such pressure is indicated by the gauge 3 or by the aforementioned riser.

The just described mode of operation of the rudimentary apparatus of FIGS. 1 and 2 is rather cumbersome because it necessitates evacuation of a certain quantity of fluid from the space 8 if the initial pressure of such fluid is excessive or the admission of fluid into the space 8 if the initial pressure does not suffice to effect at least some flattening or denting of the flexible portion 4. However, FIGS. 1 and 2 show, quite clearly, that the just described rudimentary apparatus is capable of indirectly ascertaining the pressure of fluid in the plenum chamber 5 without puncturing and/or drilling a hole into the envelope of the plenum chamber. Care should be taken to avoid deformation of the portion 4 beyond the elastic limit of its material.

The apparatus of FIGS. 1 and 2 can be operated in such a way that the space 8 receives a fluid whose pressure matches or closely approximates the pressure in a healthy human eyeball. If the flattening of a wall 6 (whose inner side is acted upon by a fluid at a pressure of 20 mm Hg) matches the flattening of the flexible portion 4, the pressure of the body 9 of fluid in the object (eyeball) 1 is satisfactory. If not, the person in charge of carrying out the test knows that the pressure of the body 9 of fluid is excessive or too low.

FIG. 3 shows a more elaborate apparatus which can be used to indirectly ascertain the pressure in an object 1 having a plenum chamber with a flexible portion 4. The apparatus comprises a first testing device 2 and a second testing device 17. The first testing device 2 comprises a housing 11 which defines a liquid-filled internal space and carries two flexible walls 6', 6" each having a convex outer side and an inner side facing the adjacent portion of the internal space. A centrally located solid partition 12 divides the internal space of the housing into two parts 2' and 2" which are respectively adjacent the inner sides of the walls 6' and 6". The means for indicating the magnitude of forces acting upon the inner sides of the walls 6' and 6" comprises two risers 3' and 3" which communicate with the respective parts 2' and 2" of the internal space of the housing 11 and are, or can be, connected to each other by a hollow yoke 10 which contains a bubble of air or another gaseous fluid. The risers 3' and 3" can also extend downwardly beyond the respective parts 2', 2" of the internal space of the housing 11 but the yoke 10 then contains a drop of a relatively heavy liquid or liquefied substance, such as mercury. The risers 3' and 3" can be replaced with gauges (note the gauge 3 of FIGS. 1 and 2) or with other suitable means for indicating the magnitude of forces acting upon the inner sides of the walls 6' and 6" in the testing device 2. The pressures at the inner and outer sides of the walls 6', 6" balance each other when the device 2 is not in use.

The housing 11 of the testing device 2 can constitute a rigid tube or cylinder the end portions of which are sealed by the respective walls 6' and 6". Each such wall can constitute a flexible membrane whose marginal portion is clamped in or otherwise sealingly secured to the respective end portion of the tubular housing 11.

The partition 12 is provided with a passage 13 which can establish communication between the parts 2' and 2" of the internal space of the housing 11 in response to partial or full lifting of a reciprocable valving element 14 which is movable up and down by a feed screw rotatable by a knob 15 or another suitable handgrip member which is accessible at the exterior of the housing 11.

In order to ensure that the testing device 2 can be moved toward or away from the flexible portion 4 of the object 1 with a minimum of friction, the housing 11 is preferably mounted on suitable friction reducing means 16, e.g., wheels or rollers which are shown in FIG. 3. Alternatively, the friction reducing means can comprise a pendulum on which the housing is suspended or a set of leaf springs on which the housing is mounted for movement to the left and to the right, as seen in FIG. 3.

The second testing device 17 of FIG. 3 comprises a rigid hollow casing 18 including a flexible wall member 19 having a convex outer side facing the convex outer side of the wall 6" and a concave or flat inner side which faces the internal compartment or space of the casing 18. Such internal space is filled with a body of fluid (e.g., a liquid), and the casing 18 is connected with a measuring instrument 20 which indirectly indicates the pressure that is applied to the outer side of the wall member 19 by indicating the pressure of fluid in the interior of the casing 18. The illustrated instrument 20 includes a riser (the fluid in the casing 18 is assumed to be a body of liquid) which is adjacent a scale calibrated to indicate the pressure of liquid in units of pressure. The casing 18 can have more than one flexible wall member.

The reference character 21 denotes an adjusting mechanism which is used to alter the pressure of fluid in the interior of the casing 18. This mechanism comprises a piston 22 which is reciprocable but does not rotate in the cylindrical right-hand portion of the casing 18 and is connected with an externally threaded piston rod 23 mating with a nut 24 which is rotatably mounted in the right-hand end wall of the casing 18. The nut 24 can be rotated by a hand wheel 25 to move the piston 22 toward or away from the wall member 19 and to thereby increase or reduce the pressure in the casing 18. If desired, the piston 22 can be replaced with a diaphragm which can be flexed toward or away from the wall member 19 by a suitable mechanism of any known design. Reference may be had to FIG. 4 which shows that the right-hand flexible wall 30 of a first testing device 26 can be deformed by a pusher 31A at the left-hand end of a reciprocable rod 31.

In order to ascertain the pressure of fluid in the plenum chamber of the object 1, the testing device 17 is moved to the left so as to advance the testing device 2 with a minimum of friction (note the aforediscussed rollers or wheels 16) whereby the wall member 19 reaches and abuts the wall 6" and the wall 6' abuts the flexible portion 4. The extent of deformation of the portion 4, walls 6', 6" and wall member 19 depends upon the pressure of fluids in the plenum chamber of the object 1, in the parts 2', 2" of the internal space of the housing 11, and in the internal space of the casing 18. It is now assumed that the pressure in the plenum chamber of the object 1 exceeds the pressure in the part 2', that the pressure in the part 2" exceeds the pressure in the casing 18 and that the pressure in the part 2" is less than the pressure in the plenum chamber. This entails a deformation of the wall 6' and wall member 19. The riser 3' indicates that the pressure in the part 2' exceeds the pressure in the part 2" (as indicated by the riser 3"). The person in charge of reading and interpreting the indications supplied by the risers 3' and 3" learns that the pressure in the plenum chamber of the object 1 exceeds the pressures in the parts 3', 3" and casing 18.

The person in charge can thereupon manipulate the adjusting mechanism 21 so as to raise the pressure of fluid in the casing 18 of the second testing device 17 until the pressure indication which is furnished by the riser 3" matches that which is furnished by the riser 3'. Such person then reads the scale next to the instrument 20 and this is indicative of pressure in the plenum chamber of the object 1.

It is important to ensure that the pressure in the parts 2' and 2" of the internal space of the housing 11 will not exceed a value which could be harmful to the object 1, especially if the object 1 is an eyeball. This can be accomplished in a simple and efficient way by properly limiting the height of the risers 3' and 3" to thus reliably prevent excessive deformation of the walls 6', 6" and eventual injury to the eye.

A presently preferred mode of operating the apparatus of FIG. 3 is as follows:

The outer side of the wall 6' is pressed against the outer side of the portion 4 of the plenum chamber in a first step. The pressure is applied until the fluid medium which fills the part 2' of the internal space of the housing 11 ascends into and can be seen in the riser 3'. In the next step, the outer side of the wall member 19 is pressed against the outer side of the wall 6" until the fluid in the part 2" of the space in the housing 11 ascends into and becomes visible in the riser 3". The second testing device 17 is urged in a direction to the left, as seen in FIG. 3, until the columns of fluid in the risers 3' and 3" reach predetermined levels (such as those indicated by the graduations a and b, respectively). If the graduations a and b are to be located at the same level, they can be omitted because the person in charge can ascertain, visually, whether or not the top surface of the column of fluid in the riser 3' is or is not at the level of the top surface of the fluid column in the riser 3".

The extent to which the volume of fluid in the internal space of the casing 18 is reduced is indicated by the instrument 20 which is calibrated in units of pressure. At such time the deforming work upon the object 1 is the same as that upon the lefthand portion of the testing device 2 (wall 6'), and the deforming work upon the right-hand portion (wall 6") of the testing device 2 is the same as that upon the testing device 17. If the indication which is furnished by the instrument 20 is influenced by (related to) the magnitude of the displaced volumes (deformations) of the parts 2' and 2"' of the testing device 2, the indications which are furnished by the instrument 20 directly denote the pressure prevailing in the object 1.

If the apparatus of FIG. 3 is used to measure the tension of an eyeball, it can be simplified by omitting the instrument 20 and the adjusting mechanism 21 provided that the pressure in the casing 18 is selected in such a way that it equals 26.66 mbar. If the riser 3' of such apparatus indicates a more pronounced reduction of the volume of the part 2' of internal space in the housing 11 than the riser 3", this automatically indicates that the tension in the eyeball is excessive. As a rule or in many instances, the second testing device 17 will be equipped with the instrument 20 and adjusting mechanism 21 because this renders it possible to actuate the mechanism 21 so as to raise the pressure in the casing 18 to such an extent that the column of fluid in the riser 3" ascends to the level of the column of fluid in the riser 3'. The instrument 20 then indicates the actual pressure in (i.e., tension of) the eyeball.

The instruments including the sensors 3' and 3" indicate a predetermined ratio of work which is performed at the walls 6' and 6" when the walls 6' and 6" are acted upon by additional forces. The fluid which acts upon the inner side of the wall member 19 opposes and balances the force acting upon the outer side of the member 19. The units of pressure in which the scale of the instrument 20 is calibrated are selected in such a way that they denote a certain proportionality to the aforementioned predetermined ratio of work performed at the walls 6' and 6". The instrument 20 is designed to furnish a signal at least when the deforming work which is performed at the walls 6', 6" is carried out at the aforementioned predetermined ratio.

FIG. 4 shows a modified apparatus for measurement of internal pressure in an object including a plenum chamber (not shown) with a flexible portion. The first testing device 26 has a rigid tubular housing which includes two deformable walls 29, 30 and is reciprocable in the casing 27 of the second testing device. The housing of the testing device 26 is biased to the left, as seen in FIG. 4, by a coil spring 28 which reacts against the right-hand end wall of the casing 27. The deformable wall member 19 of the testing device 17 of FIG. 3 is replaced with a pusher 31A at the left-hand end of a reciprocable rod 31. The spring 28 and a further spring 32 act as a sensor, and the pusher 31A is biased against the deformable wall 30 by the coil spring 32 which also reacts against the right-hand end wall of the casing 27. When a force acts on the wall 29, the difference of the lengths of the coils corresponds to the ratio of the deformations of the walls 29 and 30. The righthand end portion of the rod 31 has a set of teeth 31b mating with the teeth of a pivotable pointer 33 movable relative to a scale which is calibrated in units of pressure. The instrument including the pointer 33 indicates the difference between the extent of shifting of the first testing device 26 relative to the casing 27 and the extent of deformation of the wall 30 by the pusher 31A, and such difference is indicative of pressure in the object.

The coil spring 28 carries a sensor 28A which is movable relative to a sensor 31D on the pusher 31A. When the sensor 28A catches up with the sensor 31D in response to a predetermined deformation of the spring 28, the bias of the spring 28 is in a predetermined relationship with the pressure in the object and in the testing device 26. The sensors 28A, 31D replace the indicating instrument 3, 3' or 3"; they can generate a signal as soon as they come sufficiently close to or into actual contact with each other.

The apparatus of FIG. 4 can be operated by a patient, the same as the apparatus of FIG. 3, for example, to ascertain the tension in the eyeball.

FIG. 4a shows a modified instrument which has two pressure gauges 34', 34" and can be used in lieu of the instrument of FIG. 4, and FIG. 4b shows an additional instrument with a single gauge 34 whose pointer can be arrested at a predetermined pressure in the second testing device.

Referring to FIG. 5, there is shown a further apparatus wherein the first testing device 2 constitutes a modification of the first testing device in the apparatus of FIG. 3. The second testing device 17 is or can be identical with the second testing device of FIG. 3. The main difference is that the fluid-operated spring of FIG. 3 (which biases the inner sides of the walls 6' and 6") is replaced with a mechanical spring 35 bearing against the inner sides of the part spherical walls 6' and 6" at the respective ends of the tubular housing 11. The marginal portions of the walls 6' and 6" are secured to the respective end portions of the housing 11 which is mounted on friction reducing elements 16, the same as in the embodiment of FIG. 3. An intermediate portion of the spring 35 is in engagement with the lower end portion of a pivotable sensor in the form of an index or pointer 36 which is movable relative to a scale (note the graduation c) to indicate the extent of displacement of the respective portion of the spring 35 relative to a part of the housing 11 (e.g., relative to the fulcrum for the index 36). The graduation c is applied to a part which is carried by the housing 11. A further sensor 37 is provided to generate an optical, acoustical and/or otherwise readily detectable signal when the forces acting upon the spring 35 in a state of equilibrium are excessive.

The mode of operating the apparatus of FIG. 5 is analogous to that of operating the apparatus of FIG. 3. In the first step the wall 6' is pressed against the portion 4 of the object 1 with a force which is less than that required to cause the generation of a signal by the sensor 37. The tip of the pointer 36 travels to the left. In the next step, the testing device 17 is moved to the left so that the wall member 19 bears against the wall 6", and the movement of the testing device 17 toward the object 1 continues until the tip of the pointer 36 returns to the position of FIG. 5 (alignment with the graduation c). At such time, the reading which is furnished by the instrument 20 is indicative of pressure in the object 1.

The flexible walls 6' and 6" can be replaced with rigid walls in the form of pivotable or reciprocable plates (not shown) which are mounted in the housing 11 and are biased by suitable springs (not shown) in order to oppose the bias of the spring 35. Such springs for the plates balance the initial stress of the spring 35 and establish a state of equilibrium.

An important advantage of the improved apparatus is its simplicity. Moreover, and as mentioned above, the apparatus can be operated by a patient or by another unskilled person without extensive training. If the apparatus is used to measure the tension of eyeballs, it can be put to use without the application of anesthetics. In fact, the eyelid can be closed while the wall 6, 6' or 29 is pressed against the eye. This renders it possible to put the apparatus to use in the home of a patient or a prospective patient so that such person can contact a physician or a hospital before her or his eye or eyes undergo irreparable damage.

It is clear that the improved apparatus is susceptible of many additional modifications without departing from the spirit of the invention. For example, the instrument or instruments of the apparatus can transmit signals to electronic signal amplifying, storing and/or evaluating means as well as to means for displaying the results of measurements and/or to means for making a permanent record of the results of tests.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range. of equivalence of the appended claims.

I claim:

1. Apparatus for ascertaining the pressure in a plenum chamber which has a flexible portion, such as a tonometer for measuring the tension of an eyeball, comprising a first testing device including a housing having an internal space and comprising first and second mobile walls having outer sides and inner sides, said device further including means provided in said internal space for yieldably biasing the inner sides of said walls to counteract forces which are applied to said outer sides including a force which is applied to the outer side of said first wall when said first wall is pressured against the flexible portion of a plenum chamber, and said first device also including means for indication the magnitude of forces which act upon the inner sides of said walls; and a second testing device having mobile member operable to apply pressure to the outer side of said second wall, and means for indicating the pressure which is applied to the outer side of said second wall.

2. The apparatus of claim 1 wherein said second device comprises a hollow casing defining an internal compartment and said mobile member has a first side facing said compartment and a second side engageable with the outer side of said second wall.

3. The apparatus of claim 2, wherein said mobile member includes a membrane.

4. The apparatus of claim 1 wherein at least one of said walls includes a membrane.

5. The apparatus of claim 1, wherein said walls have substantially identical outer sides.

6. The apparatus of claim 1, further comprising means for limiting the extent of movability of at least one of said walls with reference to said housing.

7. Apparatus for ascertaining the pressure in a plenum chamber which has a flexible portion, such as a tonometer for measuring the tension of an eyeball, comprising a first testing device including a housing having an internal space and comprising first and second mobile walls having outer sides and inner sides, said device further including means provided in said internal space for yieldably biasing the inner sides of said walls to counteract forces which are applied to said outer sides including a force which is applied to the outer side of said first wall when said first wall is pressed against the flexible portion of a plenum chamber, and said biasing means comprising a mechanical spring; and a second testing device having mobile member operable to apply pressure to the outer side of said second wall, and means for indicating the pressure which is applied to the outer side of said second wall.

8. Apparatus for ascertaining the pressure in a plenum chamber which has a flexible portion, such as a tonometer for measuring the tension of an eyeball, comprising a first testing device including a housing having an internal space and comprising first and second mobile walls having outer sides and inner sides, said device further including means provided in said internal space for yieldably biasing the inner sides of said walls to counteract forces which are applied to said outer sides including a force which is applied to the outer side of said first wall when said first wall is pressed against the flexible portion of a plenum chamber, and said biasing means comprising of a fluid-operated spring; and a second testing device having a mobile member operable to apply pressure to the outer side of said second wall, and means for indicating the pressure which is applied to the outer side of said second wall.

9. Apparatus for ascertaining the pressure in a plenum chamber which has a flexible portion, such as a tonometer for measuring the tension of an eyeball, comprising a first testing device including a housing having a internal space and comprising first and second mobile walls having outer sides and inner sides, said device further including means provided in said internal space for yieldably biasing the inner sides of said walls to counteract forces which are applied to said outer sides including a force which is applied to the outer side of said first wall when said first wall is pressed against the flexible portion of a plenum chamber; and a second testing device having a mobile member operable to apply pressure to the outer side of said second wall, and means for indicating the pressure which is applied to the outer side of said second wall, said second device further comprising a hollow casing defining an internal compartment, and said mobile member having a first side facing said compartment and a second side engageable with the outer side of said second wall, said second device also comprising mechanical spring means for applying pressure to the first side of said mobile member.

10. Apparatus for ascertaining the pressure in a plenum chamber which has a flexible portion, such as a tonometer for measuring the tension of an eyeball, comprising a first testing device including a housing having an internal space and comprising first and second mobile walls having outer sides and inner sides, said device further including means provided in said internal space for yieldably biasing the inner sides of said walls to counteract forces which are applied to said outer sides including a force which is applied to the outer side of said first wall when said first wall is pressed against the flexible portion of a plenum chamber; and a second testing device having a mobile member operable to apply pressure to the outer side of said second wall, and means for indicating the pressure which is applied to the outer side of said second wall, said second device further comprising a hollow casing defining an internal compartment, and said mobile member having a first side facing said compartment and a second side engageable with the outer side of said second wall, said second device also comprising fluid-operated spring means for applying pressure to the first side of said mobile member.

11. Apparatus for ascertaining the pressure in a plenum chamber which has a flexible portion, such as a tonometer for measuring the tension of an eyeball, comprising a first testing device including a housing having an internal space and comprising first and second mobile walls having outer sides and inner sides, said device further including means provided in said internal space for yieldably biasing the inner sides of said walls to counteract forces which are applied to said outer sides including a force which is applied to the outer side of said first wall when said first wall is pressed against the flexible portion of a plenum chamber, and said internal space having a first fluid-filled part adjacent to the inner side of said first wall and a second fluid-filled part adjacent to the inner side of said second wall, said first device also comprising means for indicating the magnitude of forces acting upon the inner sides of said walls including first and second risers communciating with said first and second parts, respectively; and a second testing device having a mobile member operable to apply pressure to the outer side of said second wall, and means for indicating the pressure which is applied to the outer side of said second wall.

12. The apparatus of claim 11, wherein said means for indicating the magnitude of forces further comprises means for communicatively connecting said risers to each other outside of said housing.

13. Apparatus for ascertaining the pressure in a plenum chamber which has a flexible portion, such as a tonometer for measuring the tension of an eyeball, comprising a first testing device including a housing having an internal space and comprising first and second mobile walls having outer sides and inner sides, said device further including means provided in said internal space for yieldably biasing the inner sides of said walls to counteract forces which are applied to said outer sides including a force which is applied to the outer side of said first wall when said first wall is pressed against the flexible portion of a plenum chamber, and said biasing means comprising a spring which bears against the inner sides of said walls, said first device also comprising means for indicating the bias of said spring; and a second testing device having a mobile member operably to apply pressure to the outer side of said second wall, and means for indicating the pressure which is applied to the outer side of said second wall.

14. The apparatus of claim 13, wherein the spring is movable in said housing by said walls and said means for indicating the bias of said spring includes means for indicating changes in the position of a portion of said spring with reference to a portion of said housing.

15. Apparatus for ascertaining the pressure in plenum chamber which has a flexible portion, such as a tonometer for measuring the tension of an eyeball, comprising a first testing device including a housing having an internal space and comprising first and second mobile walls having outer sides and inner sides, said device further including means provided in said internal space for yieldably biasing the inner sides of said walls to counteract forces which are applied to said outer sides including a force which is applied to the outer side of said first wall when said first wall is pressed against the flexible portion of a plenum chamber; and a second testing device having a mobile member operable to apply pressure to the outer side of said second wall, and means for indicating the pressure which is applied to the outer side of said second wall, said second device further comprising a fluid-filled casing having a membrane-like portion constituting said mobile member, and said pressure indicating means comprising a pressure gauge calibrated to indicate the pressure of fluid in said casing in units of pressure.

16. The apparatus of claim 15, wherein said membrane-like portion has a substantially convex outer side with a radius which equals or approximates the radius of a human eyeball.

* * * * *